United States Patent
Gaylord

(10) Patent No.: US 6,852,088 B2
(45) Date of Patent: Feb. 8, 2005

(54) KNEE SUPPORT DEVICE FOR APPLYING RADIAL PRESSURE

(75) Inventor: Eric Lee Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 316 days.

(21) Appl. No.: 10/112,813

(22) Filed: Mar. 29, 2002

(65) Prior Publication Data

US 2003/0187375 A1 Oct. 2, 2003

(51) Int. Cl.[7] ................................................. A61F 5/00
(52) U.S. Cl. ........................... 602/19; 602/26; 602/62
(58) Field of Search ............................. 602/19, 26, 62, 602/5, 23, 75; 128/881, 882; 2/22, 24; 165/104.26, 104.33, 104.21, 104.4; 361/700; 257/714, 715

(56) References Cited

U.S. PATENT DOCUMENTS

| | | | |
|---|---|---|---|
| 4,334,528 A | | 6/1982 | Gauvry |
| 4,353,362 A | * | 10/1982 | DeMarco ...................... 602/26 |
| 4,777,946 A | | 10/1988 | Watanabe et al. |
| 4,833,730 A | * | 5/1989 | Nelson ............................ 2/44 |
| 4,836,194 A | * | 6/1989 | Sebastian et al. ............. 602/19 |
| D307,054 S | | 4/1990 | Johnson, Jr. |
| 5,024,216 A | * | 6/1991 | Shiono ......................... 602/26 |
| 5,038,760 A | * | 8/1991 | Osborn ........................ 602/19 |
| 5,086,759 A | * | 2/1992 | Buddingh ..................... 602/19 |
| 5,147,261 A | * | 9/1992 | Smith et al. ................. 482/106 |
| 5,399,150 A | * | 3/1995 | Saunders ...................... 602/19 |
| 5,417,646 A | | 5/1995 | Gauvry |
| 5,551,085 A | * | 9/1996 | Leighton ......................... 2/44 |
| 5,556,374 A | * | 9/1996 | Grace et al. .................. 602/26 |
| 5,560,046 A | * | 10/1996 | Iwamasa et al. .............. 2/328 |
| 5,586,969 A | * | 12/1996 | Yewer, Jr. .................... 602/19 |
| 5,591,122 A | * | 1/1997 | Yewer, Jr. .................... 602/19 |
| 5,656,023 A | * | 8/1997 | Caprio et al. ................ 602/63 |
| 5,693,006 A | * | 12/1997 | Slautterback ................ 602/19 |
| 5,865,777 A | * | 2/1999 | Detty ........................... 602/26 |
| 5,984,885 A | * | 11/1999 | Gaylord et al. ............... 602/19 |
| 6,066,108 A | * | 5/2000 | Lundberg ..................... 602/23 |
| 6,080,124 A | * | 6/2000 | Falk et al. .................... 602/26 |
| 6,336,908 B1 | * | 1/2002 | Slautterback ................ 602/19 |
| 6,342,044 B1 | * | 1/2002 | Frangi et al. ................. 602/19 |
| 6,402,712 B1 | | 6/2002 | Gauvry |
| 6,419,652 B1 | * | 7/2002 | Slautterback ................ 602/19 |
| 6,485,448 B2 | * | 11/2002 | Lamping et al. ............. 602/26 |
| 2004/0077981 A1 | * | 4/2004 | Weaver et al. ................ 602/19 |

OTHER PUBLICATIONS

Marketing material from Aircast Devices website—Printed Apr. 2, 2003 (1 page).
Marketing material from Pro–Tec Knee Support website—Printed Apr. 2, 2003 (1 page).
Marketing material from Pro Brand Sports Industries, Inc. website—Printed Apr. 2, 2003 (4 pages).
Marketing material from Brace International website—Printed Apr. 2, 2003 (1 page).
Marketing material from Cho–Pat Sport Medical Devices website—Printed Apr. 2, 2003 (1 page).

* cited by examiner

Primary Examiner—Kathryn P Odland
(74) Attorney, Agent, or Firm—Summa & Allan, P.A.

(57) ABSTRACT

An adjustable support device for the knee, including a strap having at least one elastic portion and first and second ends. A primary tensioning device is positioned on the strap for securing the strap around the knee and positioning the strap in a primary tensioned position relative to the patella, knee joint, and attachment sites of the connective tissues of the knee joint. A secondary tensioning device is also carried by the strap and includes an elastic element and at least one attachment member for being placed in a secondary tensioned position relative to the strap for increasing the tension of the strap and applying concentrated radially-directed support pressure to, the knee joint, attachment sites of the connective tissues of the knee joint, and an anterior aspect of the patella.

26 Claims, 12 Drawing Sheets

US 6,852,088 B2

KNEE SUPPORT DEVICE FOR APPLYING RADIAL PRESSURE

TECHNICAL FIELD AND BACKGROUND OF THE INVENTION

This invention relates to an adjustable support strap for use in alleviating pain associated with a variety of conditions affecting the knee. Although the support strap of the present invention is specifically intended for use by athletes to correct deficiencies in patellar tracking and to treat patellar tendonitis, the support strap is equally suited for use in treating individuals who suffer from a variety of conditions affecting the knee and who require supplemental support to relieve pain and/or preserve the mobility of the knee joint. The support strap is thus suitable for alleviating the symptoms of several conditions including, but not limited to, injuries to the anterior and posterior cruciate ligaments, the medial and lateral collateral ligaments, and injuries that cause the various muscular etiologies of patellofemoral pain syndrome.

While prior art straps and other devices exist which attempt to alleviate pain associated with the knee, knee joint and related tissues, such devices seldom apply a sufficient amount of pressure to the affected area to adequately relieve the discomfort suffered by the wearer. To the extent such devices do manage to apply any pressure to the knee, such pressure is usually distributed equally across the device and is thus inefficiently and incorrectly applied to the knee. Furthermore, the manner in which the ends of prior art straps extend around the knee, overlap each other and are connected together compromises the maximum amount of pressure the strap is actually capable of achieving and applying to the knee. This is because a small amount of the tension achieved in the strap when the strap is stretched around the knee is inevitably lost when the wearer loosens his or her grip on one end of the strap so that the other end can be connected thereto.

The present invention overcomes the inadequacies of prior art devices by providing an adjustable support strap which utilizes elastomeric materials to apply pressure to specific aspects of an injured knee. The strap is adjusted using two separate mechanisms to create two levels of tension to be applied to the knee, without sacrificing the total amount of tension created when the ends of the strap are wrapped around the knee and connected together. The support strap has a narrow end that fits through a slit that extends through the other, wider end of the strap. Once the narrow end passes through the slit, the wearer adjusts the first level of tension by grasping and pulling on each end of the strap and then attaching the ends directly to the outer surface of the strap using male hook fastener patches which cling to the outer surface of the strap. The second level of tension is then adjusted using a supplemental tensioning device that permits the wearer to apply a concentrated amount of radially-directed pressure to a specific area of the knee to relieve specific symptoms associated with that area.

SUMMARY OF THE INVENTION

Therefore, it is an object of the present invention to provide an adjustable support strap for relieving the symptoms associated with patella tendinitis and other conditions affecting the knee.

It is another object of the present invention to provide an adjustable support strap that may be adjusted without loosening or removing the strap from around the knee to alter the amount of compression applied by the strap to the knee.

It is another embodiment of the present invention to provide an adjustable support strap that is easy to position around the right or left knee, or around the leg adjacent thereto.

It is another object of the present invention to provide an adjustable support strap that can be quickly placed around and removed from the knee without difficultly and without requiring specialized medical training.

It is another object of the present invention to provide an adjustable support strap that encircles the knee and provides a consistent level of radially-directed compression around the circumference of the knee while providing an enhanced, concentrated level of compression to a preselected portion of the anatomy of the knee.

These and other objects of the invention are achieved in the preferred embodiments disclosed below by providing an adjustable support device for the knee. The device includes an elongate strap having at least one elastic portion, and first and second ends for being secured around the knee in a tensioned condition and providing supplemental support to the patella, knee joint, and attachment sites of the connective tissues of the knee joint. A primary tensioning device is positioned on the strap for securing the strap around the lower leg and positioning the strap in a primary tension position relative to the patella, knee joint, and attachment sites of the connective tissues of the knee joint. A secondary tensioning device is carried by the strap and includes an elastic element and at least one attachment member for being placed in a secondary tension position relative to the strap for increasing the tension of the strap and applying concentrated radially-directed pressure to the knee joint, attachment sites of the connective tissues of the knee joint, to the knee joint, attachment sites of the connective tissues of the knee joint, and an anterior aspect of the patella.

According to one preferred embodiment of the invention, the primary tensioning device includes first and second fasteners attached to the first and second ends, respectively, and cooperating with an outer surface of the strap for securing the strap around the lower leg and placing the strap in the primary tensioned position.

The first and second fasteners are each preferably a patch of hooked material complementary to the outer surface of the strap.

According to another preferred embodiment of the invention, the outer surface is formed from looped material complementary to the first and second fasteners.

According to yet another preferred embodiment of the invention, the primary tensioning device includes an opening defined by and extending through the strap adjacent the first end. The opening is adapted for receiving the second end of the strap therethrough, thereby permitting the tension on the strap to be increased prior to placing the strap in the primary tension position and without removing the strap from around the knee.

According to yet another preferred embodiment of the invention, the primary tensioning device includes an opening defined by and extending through the strap adjacent the second end. The opening is adapted for receiving the first end therethrough, thereby permitting tension on the strap to be increased prior to placing the strap in the primary tension position and without removing the strap from around the knee.

According to yet another preferred embodiment of the invention, the opening is an elongate slot extending perpendicularly to the longitudinal axis of the strap for permitting ease of movement of the end of the strap therethrough.

According to yet another preferred embodiment of the invention, a protective patch covers a side edge defining the opening for preventing wear to the side edge resulting from repeated placement of the end of the strap through the opening.

According to yet another preferred embodiment of the invention, the strap includes a centrally-disposed portion positioned between and integrally formed with the first and second ends for being placed over the knee joint, attachment sites of the connective tissues of the knee joint, and the anterior aspect of the patella.

According to yet another preferred embodiment of the invention, the centrally-disposed portion is defined by opposing, arcuate side edges of the strap for providing a supporting fit against the convex shape of the patella.

According to yet another preferred embodiment of the invention, the centrally-disposed portion includes a width greater than the width of each of the first and second ends for permitting pressure to be applied by the centrally-disposed portion to an increased surface area of the knee.

According to yet another preferred embodiment of the invention, the longitudinal axis of the secondary tensioning device is aligned with the longitudinal axis of the strap, thereby increasing the amount of concentrated, radially-directed support pressure applied to the knee joint, connective tissues of the knee joint, and anterior aspect of the patella.

According to yet another preferred embodiment of the invention, the strap includes interior walls defining a chamber for receiving the elastic element of the secondary tensioning device therein.

According to yet another preferred embodiment of the invention, the elastic element includes identically-shaped patches of material overlaid in registration with one another and joined together along opposing side edges.

According to yet another preferred embodiment of the invention, the secondary tensioning device includes two attachment members connected to respective opposing side edges of the elastic element and releasably connected to the outer surface of the strap for placing the secondary tensioning device in the secondary tensioned position.

According to yet another preferred embodiment of the invention, each of the attachment members is a patch of hooked material complementary to the outer surface of the strap.

According to yet another preferred embodiment of the invention, the elastic element is positioned within the chamber and is axially movable between a contracted position in the absence of tension on the elastic element and an expanded position in response to laterally-directed forces on the respective opposing side edges of the elastic element, thereby permitting the secondary tensioning device to be placed in the secondary tension position relative to the strap.

According to yet another preferred embodiment of the invention, the secondary tensioning device includes first and second pairs of ligatures interconnecting the attachment element with the elastic element for preventing loss of the attachment element when not in use.

According to yet another preferred embodiment of the invention, the first and second pairs of ligatures extend through respective pairs of openings defined in the strap, thereby permitting the elastic element to be positioned within the chamber while simultaneously permitting the attachment member to be releasably attached to the outer surface of the strap.

According to yet another preferred embodiment of the invention, a semi-rigid, elongate bar is positioned within the chamber between the elastic element and the interior wall adjacent the wearer's knee. The bar cooperates with the elastic element for directing the concentrated, radially-directed support pressure to the knee joint, attachment sites of the connective tissues of the knee joint, and the predetermined aspect of the patella.

According to yet another preferred embodiment of the invention, an adjustable support device for supporting a wearer's knee is provided that includes an elongate strap with at least one elastic portion, and first and second ends for being secured around the knee in a tensioned condition and providing supplemental support to the patella, knee joint, and attachment sites of the connective tissues of the knee joint. A primary tensioning device is positioned on the strap for securing the strap around the lower leg and positioning the strap in a primary tension position relative to the patella, knee joint, and attachment sites of the connective tissues of the knee joint. A secondary tensioning device is also included, and has at least one attachment member carried on the outer surface of the strap and connected to an elastic element positioned within a chamber defined by interior walls of the strap. The secondary tensioning device is adapted for being placed in a secondary tension position relative to the strap for increasing the tension of the strap and applying concentrated radially-directed support pressure to a knee joint, the attachment sites of the connective tissues of the knee joint, and an anterior aspect of the patella.

A preferred embodiment of a method for supporting the knee includes the step of providing an adjustable support device. The support device has an elongate strap with at least one elastic portion, an outer surface, and first and second ends for being secured around the knee in a tensioned condition and providing supplemental support to the patella, knee joint, and attachment sites of the connective tissues of the knee joint. A primary tensioning device is positioned on the strap for securing the strap around the lower leg and positioning the strap in a primary tensioned position relative to the patella, knee joint, and attachment sites of the connecting tissues of the knee joint. A secondary tensioning device is carried by the strap and includes an elastic element and at least one attachment member for being placed in a secondary tensioned position relative to the strap for increasing the tension of the strap and applying concentrated radially-directed pressure to the knee joint, attachment sites of the connective tissues of the knee joint, and an anterior aspect of the patella. The method also includes the steps of securing the strap around the knee and positioning the strap in the primary tensioned position using the primary tensioning device, and placing the secondary tensioning device in the secondary tension position, thereby increasing the tension on the strap and applying the concentrated radially-directed support pressure.

According to another preferred embodiment of a method of practicing the invention, the step of providing the adjustable support device includes the step of providing a semi-rigid, elongate bar carried by the strap intermediate the first and second ends for directing the concentrated, radially-directed support pressure to the knee joint, attachment sites of the connective tissues of the knee joint, and the anterior aspect of the patella.

According to yet another preferred embodiment of a method of practicing the invention, the step of providing the strap includes providing a chamber for receiving the elastic element of the secondary tensioning device therein.

According to yet another preferred embodiment of a method of practicing the invention, the step of providing the secondary tensioning device includes the step of positioning an elongate bar within the chamber between the elastic element and an interior wall adjacent the knee. The bar cooperates with the elastic element for directing the concentrated, radially-directed pressure to the knee joint, attachment sites of the connective tissues of the knee joint, and the anterior aspect of the patella.

According to yet another preferred embodiment of a method of practicing the invention, the step of displacing the secondary tensioning device relative to the strap is included, thereby varying the tension on the strap and redirecting the concentrated, radially-directed support pressure relative to the knee joint, attachment sites of the connective tissues of the knee joint, and the anterior aspect of the patella.

According to yet another preferred embodiment of a method of practicing the invention, the step of displacing the secondary tensioning device includes the steps of removing the secondary tensioning device from the strap, extending the length of the secondary tensioning device along the longitudinal axis thereof, and repositioning the extended secondary tensioning device on the strap.

According to yet another preferred embodiment of a method of practicing the invention, the step of extending the length of the secondary tensioning device along the longitudinal axis thereof includes applying first and second opposing, laterally-directed forces on respective first and second ends of the secondary tensioning device.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
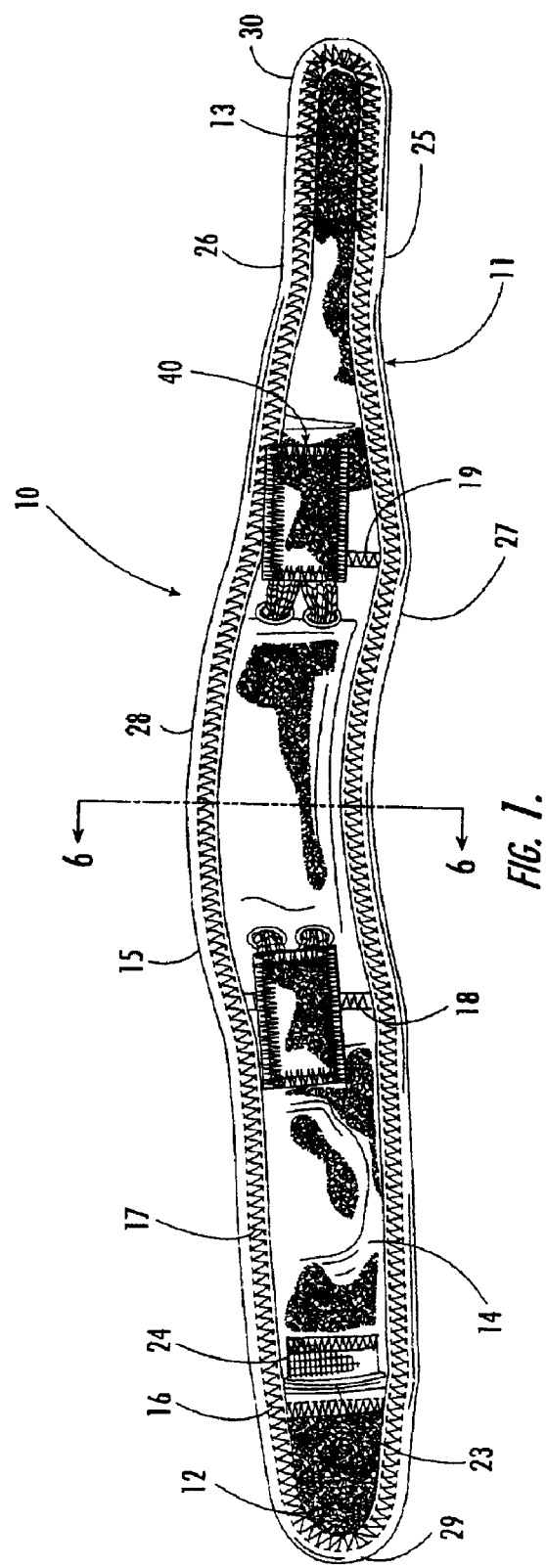
FIG. 1 is a front elevation of an adjustable patellar support strap according to one preferred embodiment of the invention.

Referring now generally to the drawings, an adjustable patellar support is illustrated in FIG. 1 and shown generally at reference numeral 10. The support 10 includes an elongate strap 11 that has first and second ends 12 and 13. The strap 11 is formed from a front panel 14 and a back panel 15 (see FIG. 2) which are overlaid with each other. The peripheral edge of panel 14 and one of the pairs of opposing side edges of back panel 15 are joined together and covered by a narrow strip of binding 16, which is preferably attached to the strap 11 using a row of zig-zag stitches 17 that extends around the perimeter of the front panel 14 adjacent the peripheral edge. Additional seams 18 and 19 formed by respective rows of zig-zag stitches extend across the width of the strap 11 and the back panel 15 to the front panel 14.

Figure 2:
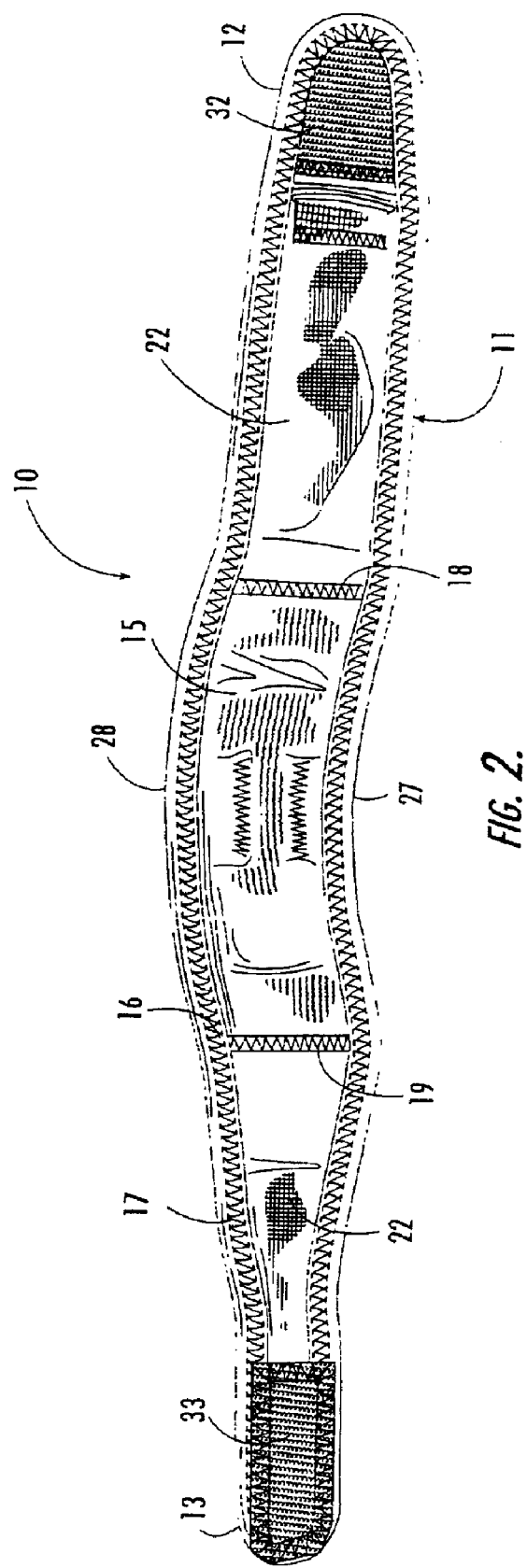
FIG. 2 is a rear elevation of the support strap according to FIG. 1.

Although the front panel 14 may be formed from any suitable material, the front panel 14 is preferably formed from a neoprene replacement material having a raised, fibrous outer surface 20, a foam core 21 (see FIG. 6), and a smooth backing material 22 (see FIG. 2). Referring again to FIG. 1, a narrow slit 23 extends through the strap 11 adjacent end 12. As described with reference to FIGS. 7 and 8 below, end 13 is placed through slit 23 when the support 10 is secured in place around the knee of the wearer. A reinforcing patch 24 of knitted material covers and protects one of the edges defining the slit 23 to prevent end 13 from causing excessive wear to the slit 21 during use.

As is shown in FIG. 1, the strap 11 is specifically contoured to fit the anatomy of the knee. In particular, the elongate shape of the strap 11 is defined by opposing side edges 25 and 26 each of which extends along the longitudinal axis of the strap 11. Side edges 25 and 26 have inwardly and outwardly curved portions 27 and 28, respectively, that complement the convexity of the patella when the support 10 is being worn. Side edges 25 and 26 extend between and interconnect rounded edges 29 and 30 to define ends 12 and 13, respectively. While each of the ends 12 and 13 has a tapered shape, the width of end 13 is narrower than the width of end 12, which permits end 13 to fit through the slit 21 when the support 10 is worn.

Referring now to FIG. 2, the back of the support 10 is shown. The back panel 15 is positioned between the curved portions 27 and 28, and is attached to the front panel 14 using stitches 17 and seams 18 and 19. Although the back panel 15 may be formed from any suitable substance, the back panel 15 is preferably formed from a neoprene replacement material identical to that used to form the front panel 14, and thus has an outer surface 32 having features identical to those of outer surface 20.

As is shown in FIG. 2, patches 32 and 33 of male hook fasteners are attached to the back surface 22 of front panel 14 adjacent ends 12 and 13, respectively. As discussed in detail below with reference to FIGS. 7 through 9, patches 32 and 33 are not only used to connect ends 12 and 13 together to hold the strap 11 in place around the wearer's knee, but are also used in cooperation with the elastic qualities of the fabric materials used to form the front and back panels 14 and 15, respectively, to vary to degree of radially-directed pressure placed by the strap 11 around the circumference of the knee. While the male hook fastener patches 32 and 33 are preferably used to attach the back surface 22 to the outer surface 20 of front panel 14, complementary snaps, hook-and-eye fasteners, or any other type of suitable fastening devices may alternatively be used. The specific manner in which the patches 32 and 33 are used to tighten or loosen the strap 11 around the knee is discussed further below with reference to FIGS. 7 through 9.

Referring again to FIG. 1, the support 10 also includes a supplemental tensioning device 40 that permits the wearer to control the extent to which a concentrated amount of additional, radially-directed pressure is applied to a specific part of the knee. The use of tensioning device 40 to apply an increased level of pressure to a selected area of the knee is discussed in detail below with reference to FIGS. 10 through 12.

Figure 3:
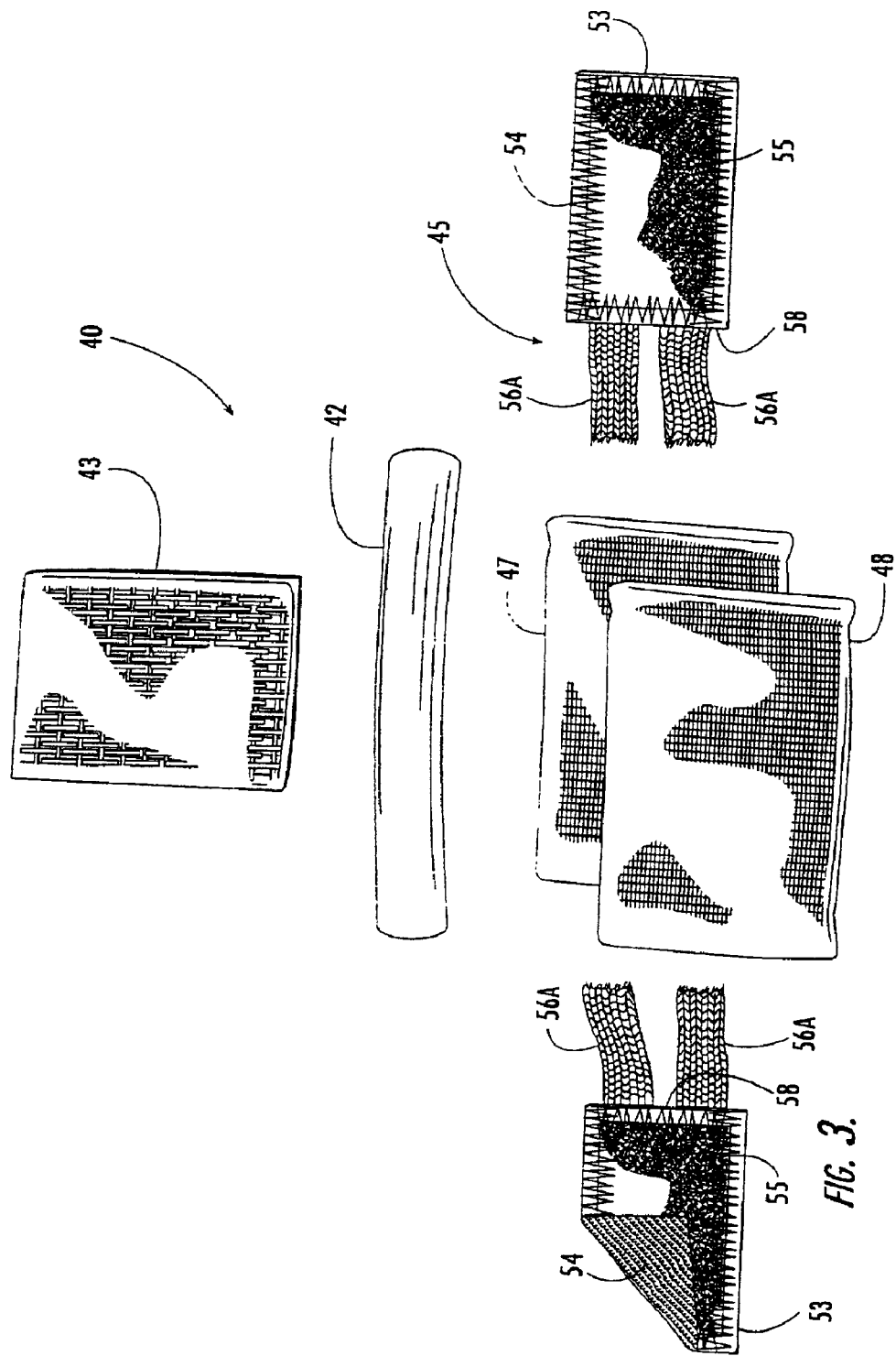
FIG. 3 is an exploded perspective view of the components of the supplemental tensioning device included in the support strap prior to assembly.

Referring now to FIG. 3, the components of the tensioning device 40 are shown. The device 40 includes a short rod 42 formed from a semi-rigid material, and a small patch 43 of knitted material. While the rod 42 is preferably a three inch length of neoprene or nylon braided cord having a ⅜ inch diameter, the rod 42 may alternatively have any suitable dimensions be formed from any suitable material, and have any cross-sectional shape. The device 40 also includes a pliable pressure applicator 45, which is capable of being stretched along its length and used to apply a radially-directed force on the rod 42, which in turn causes the rod 42 to be compressed against a predetermined area of the knee (See FIGS. 10 through 12 below). The applicator 45 includes two patches of elastomeric material 47 and 48 which are overlaid in registration with one another and sewn together along opposing side edges using seams of zig-zag stitches 49 and 50 to form a central patch 51 (See FIG. 5). Each patch 47 and 48 is preferably formed from a strip of elastic having a length of between 1.25 and 1.5 inches.

Referring again to FIG. 3, the applicator 45 also includes two fastener patches 53. Each patch 53 is preferably formed from the same material as front and back panels 14 and 15, and has an inner surface 54 covered with male hook fasteners and an outer surface 55 having a raised, fibrous texture. Two string segments 56A are connected to a side edge 58 of each patch 53. Each segment 56A may be formed from any type of string or elongate material; however, each segment 56A is preferably formed from a short length of a conventional shoelace. As described below with reference to FIG. 5, each pair of segments 56A interconnects one of the fastener patches 53 with the central patch 51.

Figure 4:
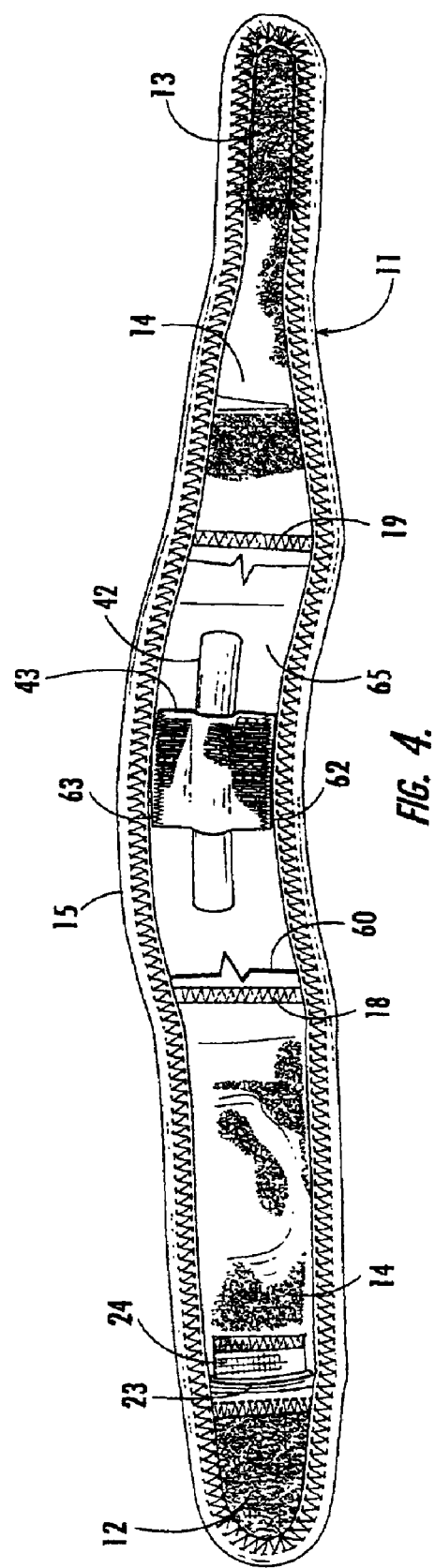
FIG. 4 is a partial cutaway view of the support strap according to FIG. 2 with part of the supplemental tensioning assembly removed.
Figure 5:
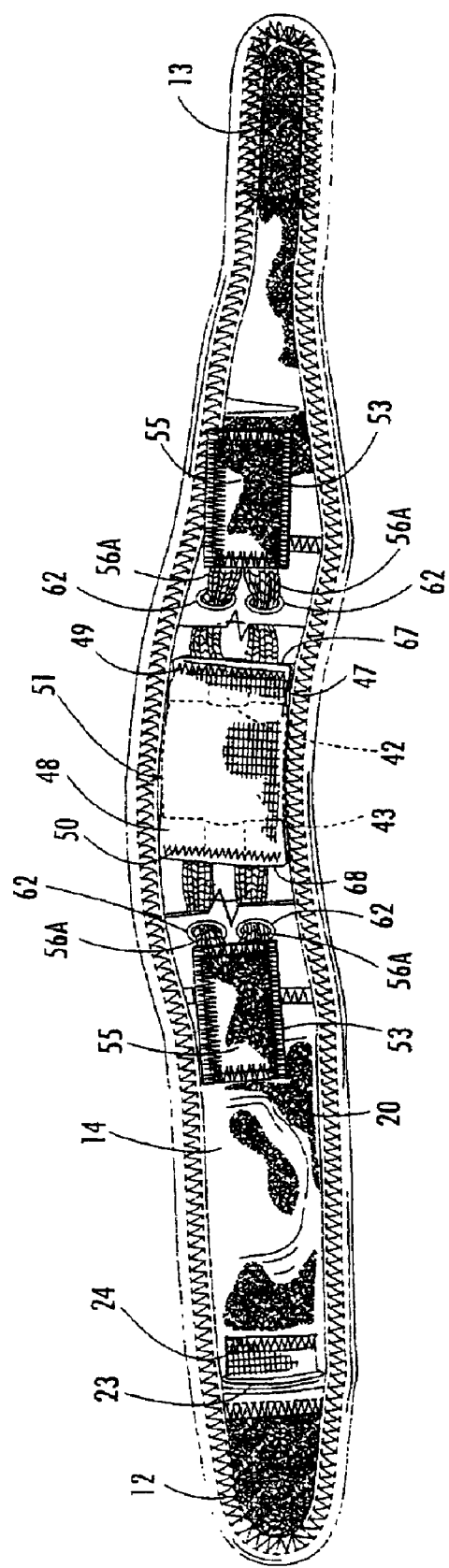
FIG. 5 is a partial cutaway view of the support strap illustrating the manner in which the components of the supplemental tensioning assembly are positioned within and relative to the exterior of the support strap.

Referring now to FIGS. 4 and 5, the manner in which the components of the supplemental tensioning device 40 are assembled and connected to the strap 11 is shown. As is shown in FIG. 4, the front and back panels 14 and 15 and seams 18 and 19 define an interior compartment 60 within which the rod 42 and patch 43 are positioned. Opposing side edges 62 and 63 of the patch 43 are attached to the inside surface 65 of the back panel 15 so that the patch 43 forms a loop 66 (See FIG. 6) through which the rod 42 is positioned.

Figure 6:
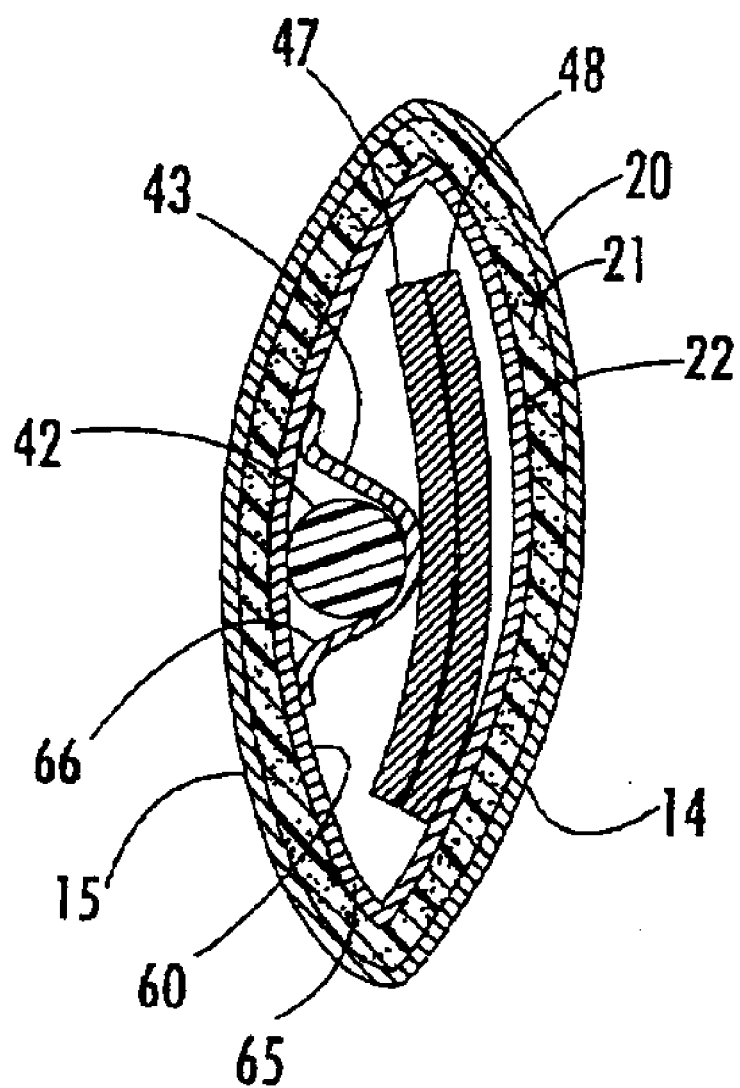
FIG. 6 is a cross-sectional view of the support strap taken along Line 6—6 of FIG. 1.

FIG. 5 shows the manner in which certain of the components of the applicator 45 are positioned within the compartment 60. The applicator 45 is assembled so that each string segment 56A extends through one of four eyelets 62 located on the front panel 14. One end of each string segment 56A is sandwiched between the elastomeric patches 47 and 48 so that two of the segments 56A are attached to each one of two opposing side edges 67 and 68, respectively. Side edges 67 and 68 are then sewn together to form the central patch 51. The other ends of each pair of string elements 56A extend to the outside of the front patch 14 and are connected to side edge 58 of one of the two fastener patches 53. As is shown in FIG. 5, the central patch 51 is positioned within compartment 60 so that it directly overlies the rod 52 and patch 53. This orientation is also shown in FIG. 6, and results in an increased application of force by the central patch 51 on the rod 52 when the pressure applicator 45 is being adjusted relative to the strap 11 (See FIGS. 10 through 12).

Figure 7:
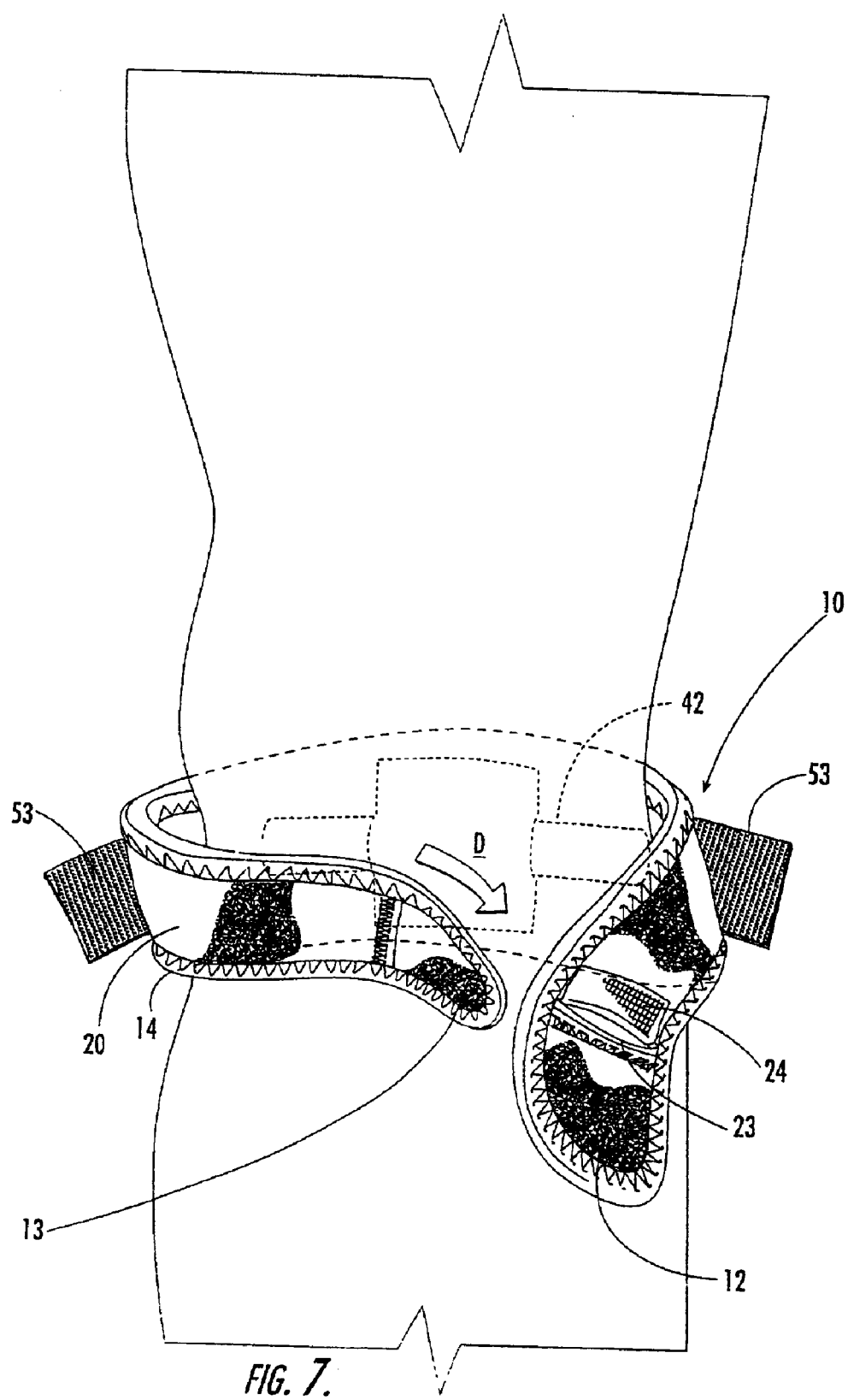
FIGS. 7 through 9 are each environmental perspective views of the support strap illustrating the manner in which the support strap is positioned around the knee and secured in place relative thereto.
Figure 8:
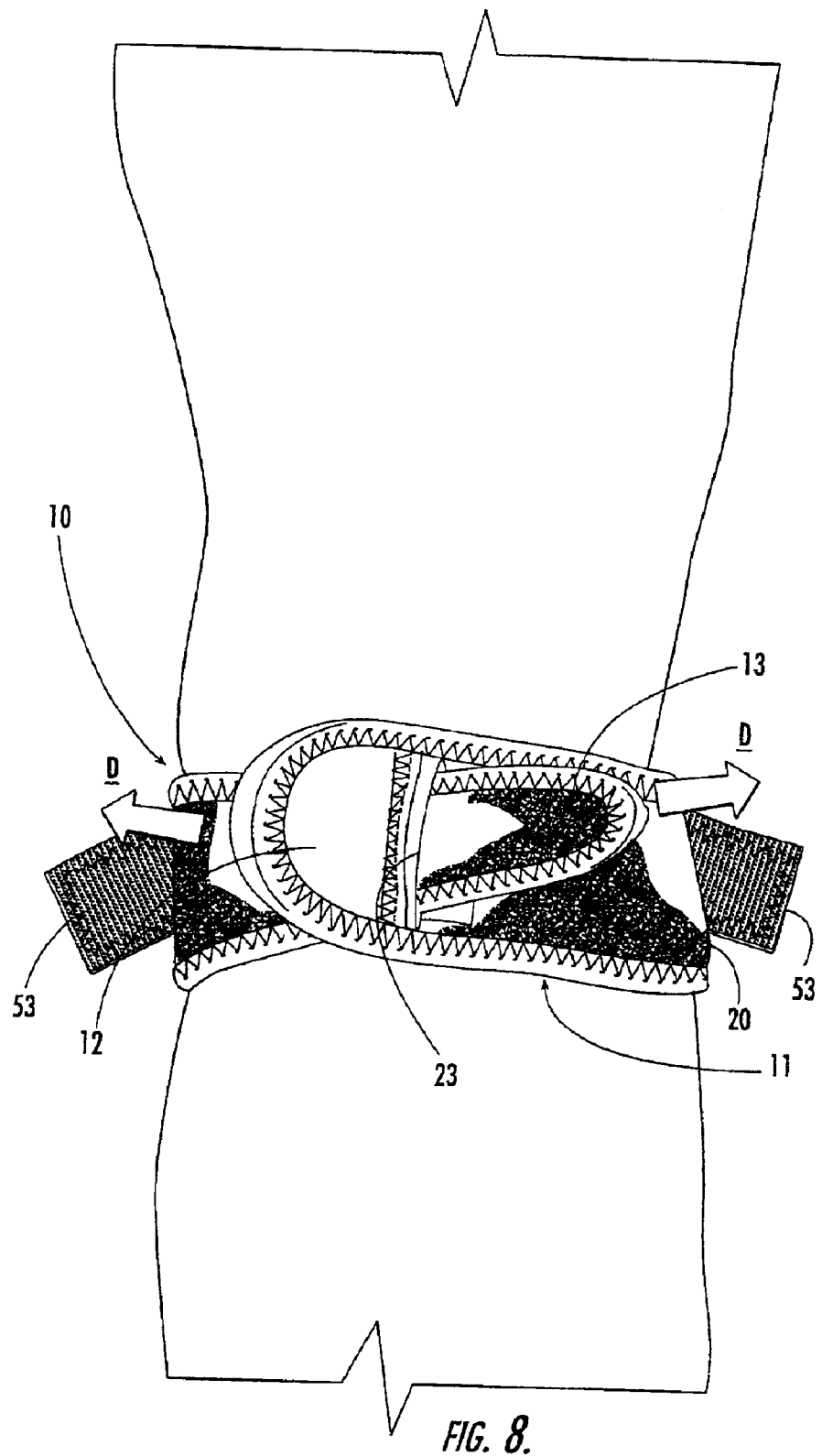
Figure 9:
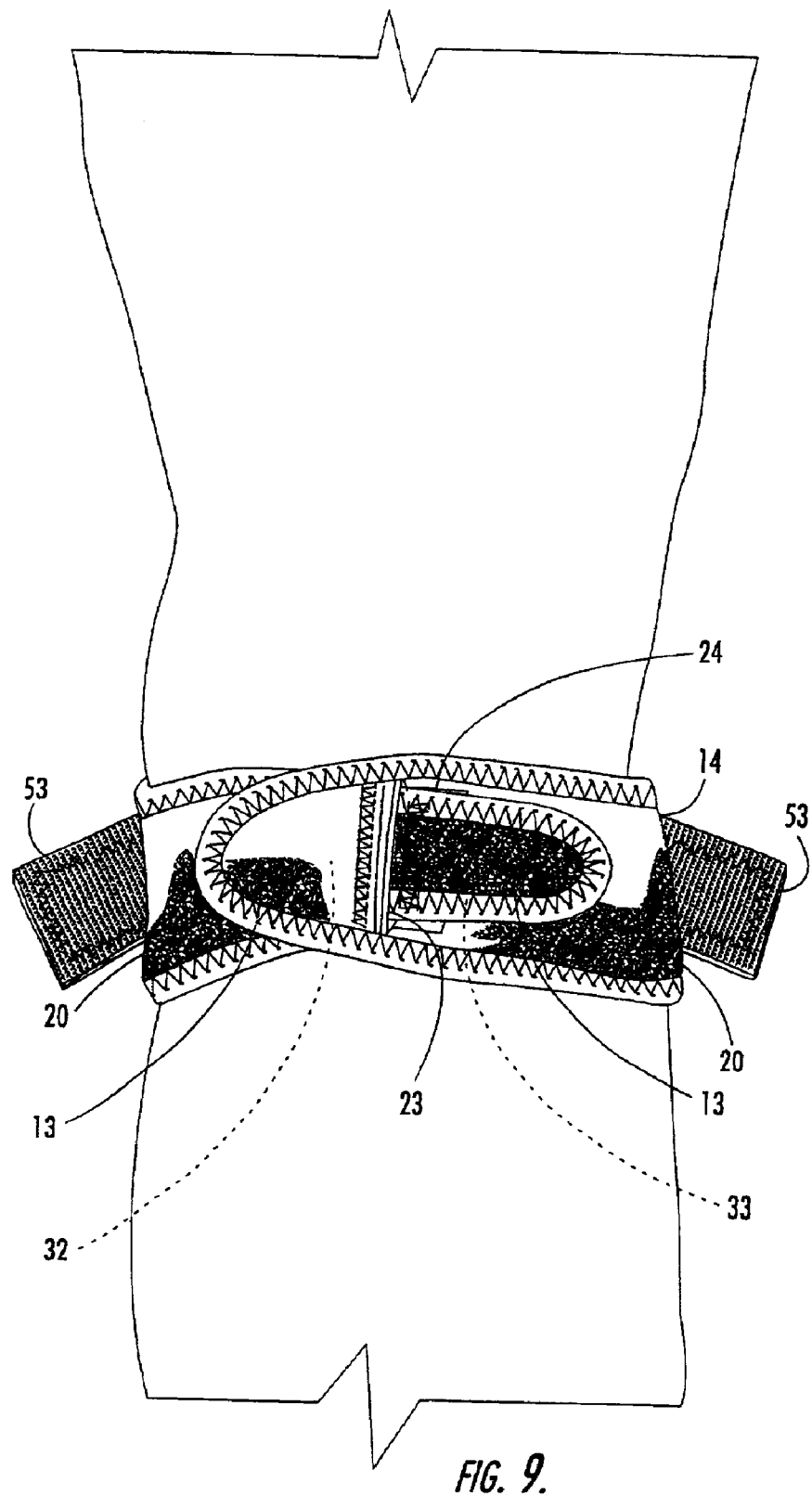

Referring now to FIGS. 7 through 12, the manner in which the support 10 is positioned around the knee of a wearer and adjusted to ensure a proper fit and application of the correct amount of pressure to the affected areas of the knee is shown. As is shown in FIG. 7, to place the support 10 around the knee, the patches 53 are released from the outer surface 20 of the front panel 14, and the strap is positioned around the knee so that the rod 42 overlies that area of the knee to which supplemental pressure is to be applied. End 13 of the strap 11 is moved toward end 12 in the direction "D" shown and, as is shown in FIG. 8, is placed through the slit 23. The ends 12 and 13 are then pulled away from each other in the opposing directions "D" shown in FIG. 8 until the desired fit and tension of the strap 11 around the knee is achieved. As is shown in FIG. 9, the ends 12 and 13 are then attached to the outer surface 20 of the front face 14 using respective fastener patches 32 and 33.

Figure 10:
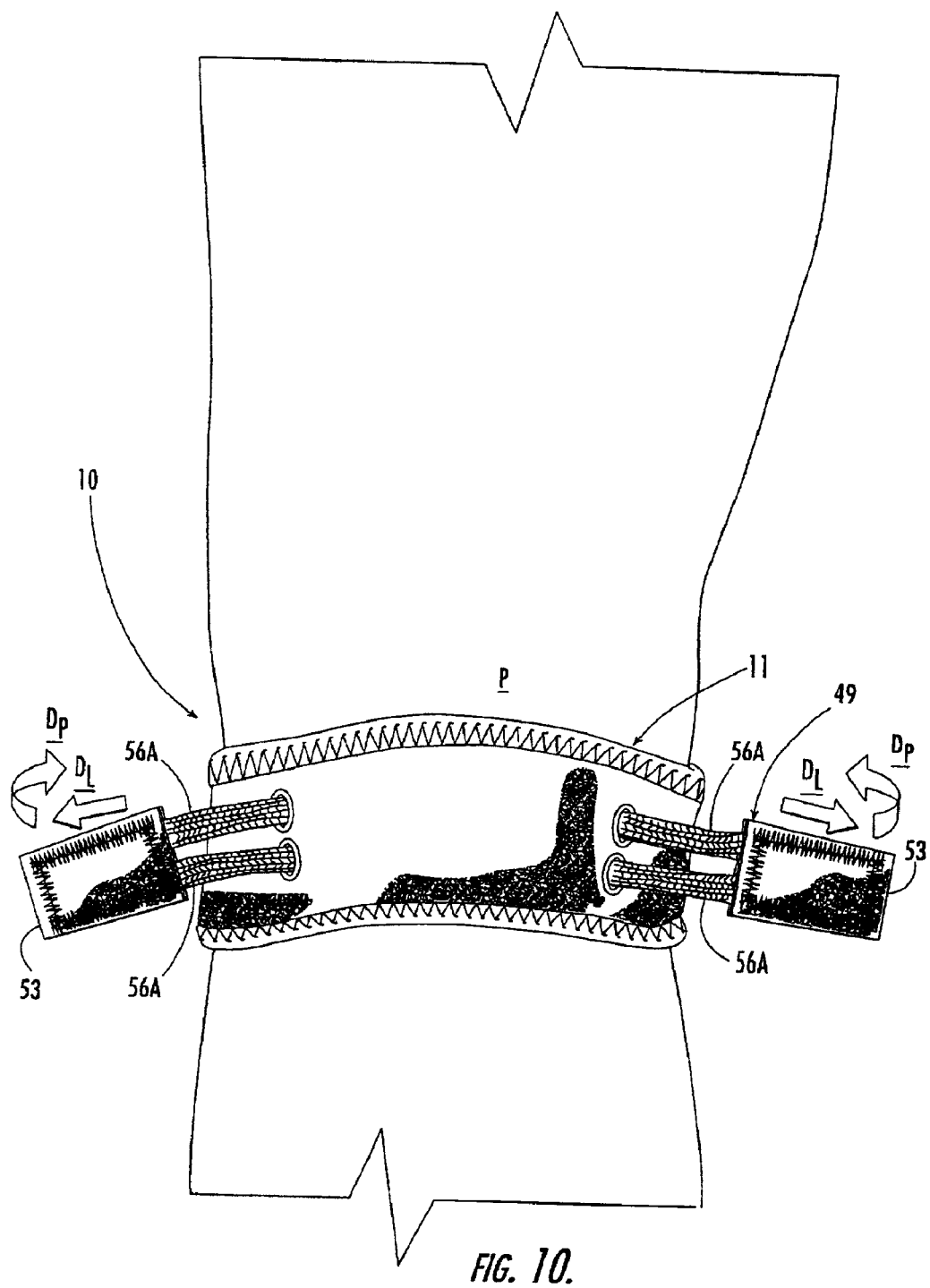
FIGS. 10 through 12 are each environmental perspective views of the support strap illustrating the manner in which the supplemental tensioning device is used to apply a concentrated degree of pressure on a specific area of the knee.
Figure 11:
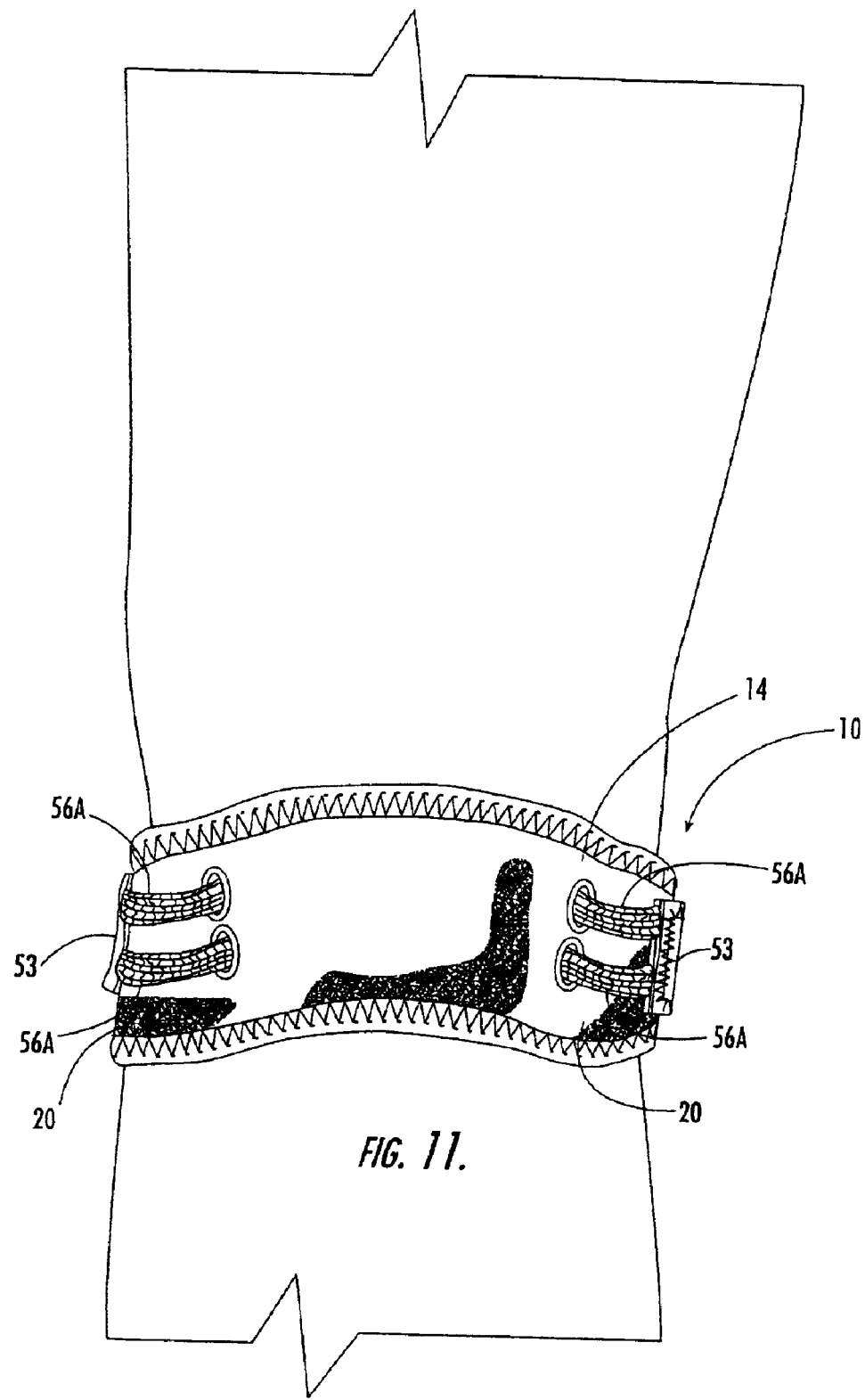
Figure 12:
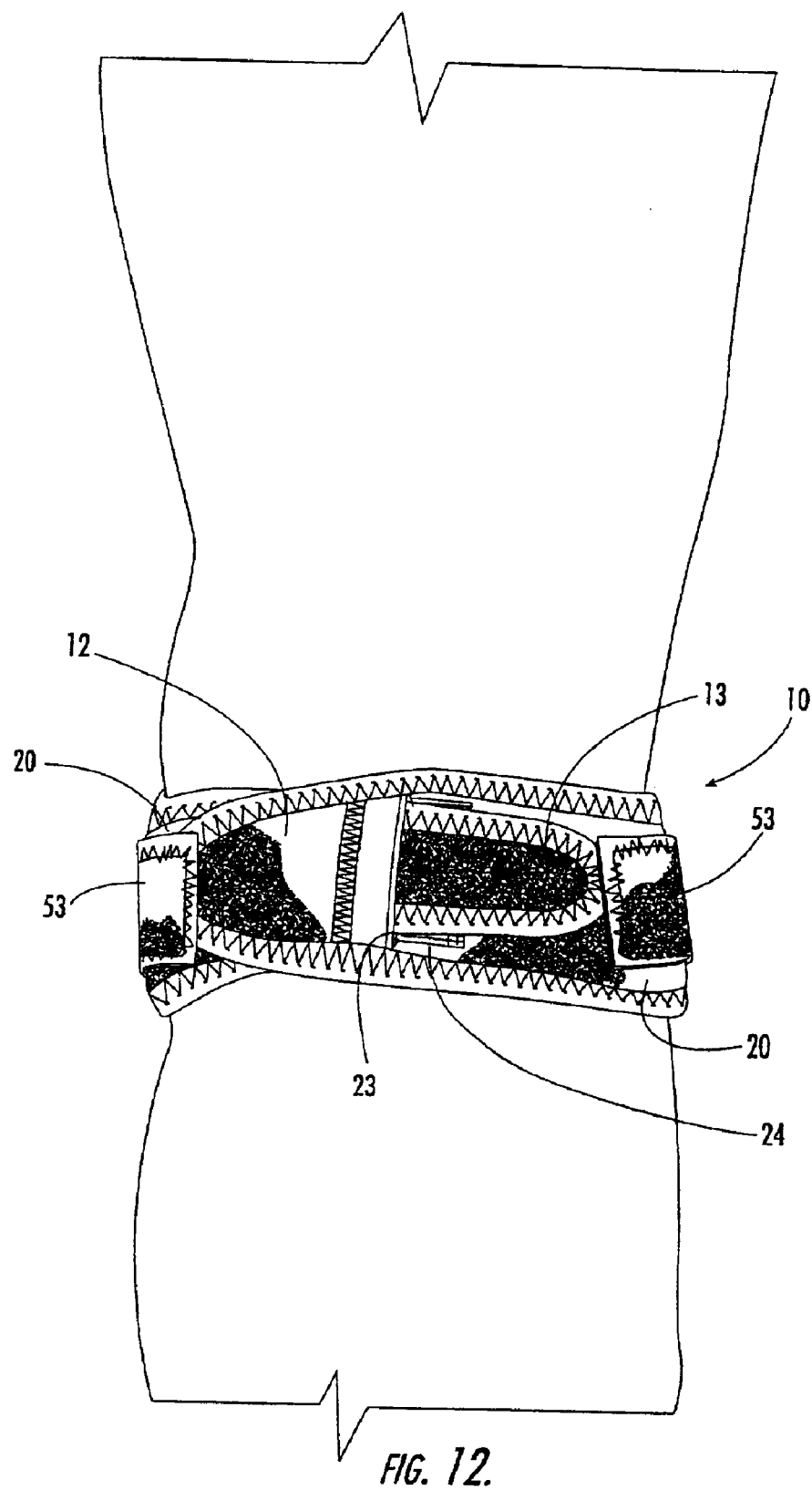

Referring now to FIG. 10, once the strap 11 is positioned around the knee, the supplemental tensioning device 40 is adjusted by first pulling each of the patches 53 in a lateral direction "DL" away from the patella, and then pulling the patches 53 toward the posterior region of the knee in the posterior direction "DP" shown. Pulling the patches 53 away from each other and then towards the anterior region of the knee causes each patch 53 to assert a force on the pair of string segments 56A to which the patch 53 is connected. This force, or tension translates to the central patch 51, which in turn stretches and expands in length within compartment 60. The expansion of the central patch 51 generates a force on the rod 42 which causes the rod 42 to bend and exert a radially-directed force on the injured area of the knee, which in turn relieves the wearer of the painful symptoms that necessitated the use of the support 10. As is shown in FIGS. 11 and 12, once the patch 51 has been stretched and the desired tension achieved, the patches 53 are reattached to the outer surface 20 of the front panel 14.

An adjustable patellar tensioning strap is described above. Various details of the invention may be changed without departing from its scope. Furthermore, the foregoing description of the preferred embodiment of the invention and the best mode for practicing the invention are provided for the purpose of illustration only and not for the purpose of limitation.

I claim:

1. An adjustable support device for the knee, comprising:
   (a) an elongate strap including at least one elastic portion, and first and second ends for being secured around the knee in a tensioned condition and providing supplemental support to the patella, knee joint, and attachment sites of the connective tissues of the knee joint, said strap having interior walls that define a chamber;
   (b) a primary tensioning device positioned on said strap for securing the strap around the knee and positioning the strap in a primary tensioned position relative to the patella, knee joint, and attachment sites of the connective tissues of the knee joint; and
   (c) a secondary tensioning device carried by the strap and including an elastic element and at least one attachment member for being placed in a secondary tensioned position relative to the strap for increasing the tension of the strap and applying concentrated radially-directed support pressure to the knee joint, attachment sites of the connective tissues of the knee joint, and an anterior aspect of the patella;
   wherein said elastic element of the secondary tensioning device is positioned within the chamber such that the elastic element is axially movable independent of said strap and said primary tensioning device between a contracted position in the absence of tension on the elastic element and an expanded position in response to laterally-directed forces on the respective opposing side edges of the elastic element, thereby permitting the secondary tensioning device to be placed in the secondary tensioned position relative to the strap.

2. A support device according to claim 1, wherein said primary tensioning device comprises first and second fasteners attached to said first and second ends, respectively, and cooperating with an outer surface of the strap for securing the strap around the knee and placing the strap in said primary tensioned position.

3. A support device according to claim 2, wherein the first and second fasteners each comprise a patch of hooked material complementary to said outer surface of the strap.

4. A support device according to claim 3, wherein the outer surface of the strap comprises looped material complementary to the first and second fasteners.

5. A support device according to claim 2, wherein the primary tensioning device further comprises an opening defined by and extending through the strap adjacent the first end, said opening adapted for receiving the second end of the strap therethrough, thereby permitting the tension on the strap to be increased prior to placing the strap in the primary tensioned position and without removing the strap from around the knee.

6. A support device according to claim 2, wherein the primary tensioning device further comprises an opening defined by and extending through the strap adjacent the second end, said opening adapted for receiving the first end therethrough, thereby permitting tension on the strap to be increased prior to placing the strap in the primary tensioned position and without removing the strap from around the knee.

7. A support device according to claim 5 or 6, wherein said opening comprises an elongate slot extending perpendicularly to the longitudinal axis of the strap for permitting ease of movement of the end of the strap therethrough.

8. A support device according to claim 5 or 6, and including a protective patch covering a side edge defining the opening for preventing wear to said side edge resulting from repeated placement of the end of the strap through the opening.

9. A support device according to claim 1, wherein said strap includes a centrally-disposed portion positioned between and integrally formed with the first and second ends for being placed over the knee joint, attachment sites of the connective tissues of the knee joint, and the predetermined anterior aspect of the patella.

10. A support device according to claim 9, wherein said centrally-disposed portion is defined by opposing, arcuate side edges of the strap for providing a supporting fit against the convex shape of the patella.

11. A support device according to claim 9 or 10, wherein said centrally-disposed portion includes a width greater than the width of each of the first and second ends for permitting pressure to be applied by the centrally-disposed portion to an increased surface area of the knee.

12. A support device according to claim 1, wherein the longitudinal axis of said secondary tensioning device is aligned with the longitudinal axis of the strap, thereby increasing the amount of concentrated radially-directed support pressure applied to the knee joint, connective tissues of the knee joint, and anterior aspect of the patella.

13. A support device according to claim 1, wherein said elastic element comprises identically-shaped patches of material overlaid in registration with one another and joined together along opposing side edges.

14. A support device according to claim 1, wherein said secondary tensioning device includes two attachment members connected to respective opposing side edges of the elastic element and releasably connected to the outer surface.

15. A support device according to claim 14, wherein each of said attachment members comprises a patch of hooked material complementary to the outer surface of the strap.

16. A support device according to claim 15, wherein the outer surface of the strap comprises looped material.

17. A support device according to claim 1, wherein said secondary tensioning device includes first and second pairs of ligatures interconnecting the attachment element with the elastic element for preventing loss of the attachment element when not in use.

18. A support device according to claim 17, wherein said first and second pairs of ligatures extend through respective first and second pairs of openings defined in the strap, thereby permitting the elastic element to be positioned within the chamber while simultaneously permitting the attachment member to be releasably attached to the outer surface of the strap.

19. A support device according to claim 1, and including a semi-rigid, elongate bar carried on the strap intermediate the first and second ends for directing the concentrated, radially-directed support pressure to the knee joint, attachment sites of the knee joint, and the anterior aspect of the patella.

20. A support device according to claim 1, and including a semi-rigid, elongate bar positioned within the chamber between the elastic element and the interior wall adjacent the knee, said bar cooperating with the elastic element for directing the concentrated, radially-directed pressure to the knee joint, attachment sites of the connective tissues of the knee joint, and the anterior aspect of the patella.

21. An adjustable support device for the knee, comprising:

(a) an elongate strap including at least one elastic portion, and first and second ends for being secured around the knee in a tensioned condition and providing supplemental support to the patella, knee joint, and attachment sites of the connective tissues of the knee joint;

(b) a primary tensioning device positioned on said strap, respectively, for securing the strap around the knee and positioning the strap in a primary tension position relative to the patella, knee joint, and attachment sites of the connective tissues of the knee joint; and (c) a secondary tensioning device including at least one attachment member carried on an outer surface of the strap and connected to an elastic element positioned within a chamber defined by interior walls of the strap, said secondary tensioning device for being placed in a secondary tensioned position relative to the strap for increasing the tension of the strap and applying concentrated radially-directed support pressure to the knee joint, attachment sites of the connective tissues of the knee joint, and the anterior aspect of the patella;

wherein said elastic element is axially movable independent of said strap and said primary tensioning device between a contracted position in the absence of tension on the elastic element and an expanded position in response to laterally-directed forces on the respective opposing side edges of the elastic element, thereby permitting the secondary tensioning device to be placed in the secondary tensioned position relative to the strap.

22. A method of supporting the knee, comprising the steps of:
- (a) providing an adjustable support device, including:
  - (i) an elongate strap having at least one elastic portion, and first and second ends for being secured around the knee in a tensioned condition and providing supplemental support to the patella, knee joint, and attachment sites of the connective tissues of the knee joint;
  - (ii) a primary tensioning device positioned on said strap for securing the strap around the knee and positioning the strap in a primary tensioned position relative to the patella, knee joint, and attachment sites of the connecting tissues of the knee joint; and
  - (iii) a secondary tensioning device carried by the strap and including an elastic element and at least one attachment member for being placed in a secondary tensioned position relative to the strap for increasing the tension of the strap and applying concentrated radially-directed pressure to the knee joint, attachment sites of the connective tissues of the knee joint, and an anterior aspect of the patella, wherein the elastic element is axially movable independent of the strap and the primary tensioning device;
- (b) securing the strap around the knee and positioning the strap in said primary tensioned position using said primary tensioning device;
- (c) placing said secondary tensioning device in said secondary tensioned position, thereby increasing the tension on the strap and applying the concentrated radially-directed support pressure;
- (d) displacing the secondary tensioning device relative to the strap;
- (e) extending the length of the secondary tensioning device along the longitudinal axis thereof to thereby apply first and second opposing, laterally-directed forces on respective first and second ends of the secondary tensioning device; and
- (f) repositioning the extended secondary tensioning device on the strap.

23. A method according to claim 22, wherein the step of providing said adjustable support device includes the step of providing a semi-rigid, elongate bar carried by the strap intermediate the first and second ends for directing the concentrated, radially-directed support pressure to the knee joint, attachment sites of the connective tissues of the knee joint, and the anterior aspect of the patella.

24. A method according to claim 22, wherein the step of providing the strap includes providing a chamber for receiving the elastic element of the secondary tensioning device therein.

25. A method according to claim 24, wherein the step of providing the secondary tensioning device includes the step of positioning an elongate bar within said chamber between the elastic element and an interior wall adjacent the knee and cooperates with the elastic element for directing the concentrated, radially-directed pressure to the knee joint, attachment sites of the connective tissues of the knee joint, and the anterior aspect of the patella.

26. A method of supporting the knee, comprising the steps of:
- (a) providing an adjustable support device, including:
  - (i) an elongate strap having at least one elastic portion, and first and second ends for being secured around the knee in a tensioned condition and providing supplemental support to the patella, knee joint, and attachment sites of the connective tissues of the knee joint;
  - (ii) a primary tensioning device positioned on said strap for securing the strap around the knee and positioning the strap in a primary tensioned position relative to the patella, knee joint, and attachment sites of the connecting tissues of the knee joint; and
  - (iii) a secondary tensioning device carried by the strap and including at least one attachment member connected to an elastic element positioned within a chamber defined by interior walls of the strap, said secondary tensioning device for being placed in a secondary tensioned position relative to the strap for increasing the tension of the strap and applying concentrated radially-directed pressure to the knee joint, attachment sites of the connective tissues of the knee joint, and an anterior aspect of the patella, said elastic element axially movable independent of the strap and the primary tensioning device between a contracted position in the absence of tension on the elastic element and an expanded position in response to laterally-directed forces on the respective opposing side edges of the elastic element, thereby permitting the secondary tensioning device to be placed in the secondary tensioned position relative to the strap;
- (b) securing the strap around the knee and positioning the strap in said primary tensioned position using said primary tensioning device; and
- (c) placing said secondary tensioning device in said secondary tensioned position, thereby increasing the tension on the strap and applying the concentrated radially-directed support pressure.

* * * * *